(12) United States Patent
Wright

(10) Patent No.: US 9,040,001 B2
(45) Date of Patent: May 26, 2015

(54) MICROTITER PLATE TEMPERATURE CONTROL

(71) Applicant: Lloyd Wright, Hopewell Junction, NY (US)

(72) Inventor: Lloyd Wright, Hopewell Junction, NY (US)

(73) Assignee: Solid State Cooling Systems, Wappingers Falls, NY (US)

( * ) Notice: Subject to any disclaimer, the term of this patent is extended or adjusted under 35 U.S.C. 154(b) by 21 days.

(21) Appl. No.: 13/856,409

(22) Filed: Apr. 3, 2013

(65) Prior Publication Data

US 2014/0134081 A1    May 15, 2014

Related U.S. Application Data

(60) Provisional application No. 61/619,597, filed on Apr. 3, 2012.

(51) Int. Cl.
| | | |
|---|---|---|
| *B01L 7/00* | (2006.01) | |
| *B01L 7/02* | (2006.01) | |
| *B01L 9/00* | (2006.01) | |
| *G01N 35/02* | (2006.01) | |
| *G01N 35/00* | (2006.01) | |

(52) U.S. Cl.
CPC . *B01L 7/50* (2013.01); *B01L 9/523* (2013.01); *G01N 35/028* (2013.01); *B01L 2300/0829* (2013.01); *B01L 2300/185* (2013.01); *G01N 2035/00396* (2013.01)

(58) Field of Classification Search
USPC .................................. 422/551–553, 939–943
See application file for complete search history.

(56) References Cited

U.S. PATENT DOCUMENTS

| | | | | |
|---|---|---|---|---|
| 3,534,430 | A | * | 10/1970 | Kesling et al. ..................... 16/34 |
| 5,171,372 | A | * | 12/1992 | Recine, Sr. ..................... 136/203 |
| 5,342,581 | A | * | 8/1994 | Sanadi ........................... 422/552 |
| 5,504,007 | A | * | 4/1996 | Haynes ....................... 435/285.1 |
| 5,508,197 | A | * | 4/1996 | Hansen et al. ............. 435/285.1 |
| 6,051,439 | A | * | 4/2000 | Antonenko et al. ............ 506/30 |
| 6,171,555 | B1 | * | 1/2001 | Cargill et al. ................. 422/560 |
| 2002/0094533 | A1 | * | 7/2002 | Hess et al. ........................ 435/6 |
| 2002/0137199 | A1 | * | 9/2002 | Jobin et al. ................. 435/287.2 |
| 2004/0110212 | A1 | * | 6/2004 | McCormick et al. ............. 435/6 |
| 2009/0098593 | A1 | * | 4/2009 | Ehrhardt et al. ................ 435/29 |
| 2009/0173472 | A1 | * | 7/2009 | Schryver et al. ................ 165/47 |
| 2010/0203595 | A1 | * | 8/2010 | Ward et al. ................... 435/91.2 |

* cited by examiner

*Primary Examiner* — Paul Hyun
*Assistant Examiner* — Robert Eom
(74) *Attorney, Agent, or Firm* — Joseph P. Kincart; Ideation Law, PLLC

(57) ABSTRACT

The present invention provides methods and apparatus for efficiently providing accurate temperature control of a microtiter cold plate and precise alignment of the microtiter cold plate with a microtiter plate.

18 Claims, 5 Drawing Sheets

MICROTITER PLATE TEMPERATURE CONTROL

CROSS REFERENCE TO RELATED APPLICATIONS

The present application claims priority to U.S. Provisional Patent Application Ser. No. 61/619,597, entitled Microtiter Plate Temperature Control, and filed Apr. 3, 2012, as a Non-Provisional Utility Patent Application, the contents of which are relied upon and incorporated herein by reference.

FIELD OF THE INVENTION

The present invention relates to an improved microtiter control plate and to methods and apparatus used control a temperature of a microtiter plate. More specifically, the present invention provides microtiter plates including precise vertical alignment for facilitating use with robotic arms.

BACKGROUND

The microtiter plate has become a standard tool in analytical research and clinical diagnostic testing laboratories. A very common usage is in the enzyme-linked immunosorbent assay ELISA, the basis of most modern medical diagnostic testing in humans and animals. Other uses include growth and analysis of bacterial or fungi cultures, DNA purification, soil analysis, fermentation studies, and other small-scale biochemical processes. Microtiter plates enable the testing of many small volume samples at one time, shortening the analysis process time and greatly reducing the amount of sample required. The later is particularly critical as the cost of the sample materials is often quite high.

Typically, microtiter plates are used in automated testing equipment, where robotic arms place microtiter plates onto a flat stage. Another robot then dispenses small quantities of one or both of chemicals and cultures which will undergo testing, into each small well. It is common for each well to have slightly different mixtures. The small size of each well makes it conducive to have precise alignment of the microtiter plate to the robotic arms.

In many of the microtiter plate uses, it is desirable to control the temperature of the sample as the contents are either temperature sensitive, or in the case of bacterial or fungi cultures, grow at rates that change exponentially with temperature. Various methods for controlling microtiter plate temperature have been tried, such as immersing the microtiter plate in a circulating fluid, blowing a heated or cooled air over the microtiter plate surface, and placing it on a heated or cooled plate.

The first two methods have serious drawbacks. Immersing a microtiter plate in a circulating fluid is problematic for two reasons: first, the microtiter plates are made from low density materials and tend to float, and second, the coolant can get into the wells, contaminating the sample. Blowing air over the microtiter plate surface has similar problems with potential contamination and, due to the low thermal mass of air, precise temperature control over the microtiter plate surface is nearly impossible.

It has been known to insert a microtiter plate into a heated or cooled cold plate to solve these problems, but a new problem arises when the microtiter plate temperature must be maintained below the ambient dew point: condensation of moisture. Minimizing condensation requires insulating all but the top surface of the cold plate with a plastic or foam insulation, which in turn creates still a new problem: alignment of the microtiter plate. It is very difficult to precisely machine or cut plastic or foam insulation. As a result, it is very difficult to maintain an insulated cold plate's precise thickness and a parallelism between a plastic base and metallic top surface. This imprecision leads to positional variation across the cold plate surface relative to the cold plate's mounting base which in turn creates problems for alignment of robotic arms that commonly load the microtiter plates onto the cold plate.

SUMMARY

Accordingly, the present invention provides improved methods and apparatus for temperature control of a microtiter plate, and in some specific embodiments, an improved microtiter cold plate is described.

According to the present invention, a microtiter cold plate is provided with one or more of: a flat metallic top surface that accepts microtiter plates from a human or robotic arm; internal fluid channels through which a constant temperature coolant flows; an insulating cover over all but the top side that minimizes condensation on the cold plate's sides and bottom; and small positioning legs that extend from the metallic cold plate through the insulated bottom to allow for precise vertical alignment. Precise vertical alignment is particularly useful when the microtiter plate is used in conjunction with robotic arms for positioning the microtiter plate.

DESCRIPTION OF THE DRAWINGS

As presented herein, various embodiments of the present invention will be described, followed by some specific examples of various components that can be utilized to implement the embodiments. The following drawings facilitate the description of some embodiments.

DETAILED DESCRIPTION

Overview

The present invention provides an improved cold plate for maintaining a temperature of a microtiter plate. According to the present invention, a microtiter plate may be placed on a Cold Plate for temperature regulation by automation, such as a robot. The automation may place a microtiter plate with great precision and the cold plate may receive the microtiter plate with precision due to the improved design of the present invention.

Definitions

"Cold Plate" or "Microtiter Cold Plate' as used herein shall mean a temperature plate of precise dimensions to receive a Microtiter Plate via mechanical automation and maintain a received Microtiter Plate a predetermined temperature.

"Microtiter Plate" as used herein, a microtiter plate, sometimes referred to as a "microplate", is a flat plate with multiple "wells" used as small test tubes. Microtiter plates may, by way of non-limiting example, measure 128 mm×85 mm and are usually made from a plastic such as polypropylene, polycarbonate, or polystyrene. A microplate typically has 96 or 384 sample wells, with some may have 9600 wells, or more. The wells are typically arranged in a 2:3 rectangular matrix.

Each microtiter plate well is capable of containing a very small volume of liquid, typically. Volumes may range, for example, from about between tens of nanoliters to about a few milliliters.

Figure 1:
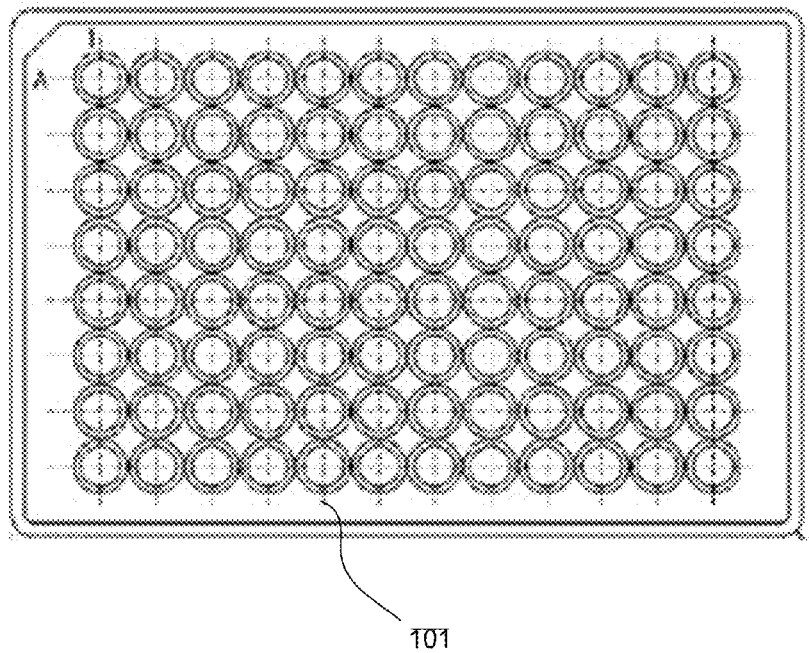
FIG. 1 illustrates a prior art microtiter plate.

Referring now to FIG. 1, a microtiter plate 100 is illustrated; the microtiter plate 100 has become a standard tool in analytical research and clinical diagnostic testing laboratories. A very common usage is in the enzyme-linked immunosorbent assay ELISA, the basis of most modern medical diagnostic testing in humans and animals. Other uses include growth and analysis of bacterial or fungi cultures, DNA purification, soil analysis, fermentation studies, and other small-scale bio-chemical processes. Microtiter plates 100 enable the testing of many small volume samples at one time, shortening analysis process time and greatly reducing the amount of sample material required. The latter is particularly important as the cost of the sample materials is often quite high. Typically, microtiter plates 100 are used in automated testing equipment, where automation, such as, for example, a robotic arm, places microtiter plates onto a flat stage.

Additional automation, such as, for example, another robot may then dispense small quantities of one or more of: chemicals; cultures; and active agents undergoing test into a plurality of the small wells 101. It is common for each well 101 to have slightly different mixtures. The relatively small size of each well requires precise alignment of the microtiter plate in relation to the robotic arm in order for the robotic arm to accurately place the microtiter plate.

Figure 2:
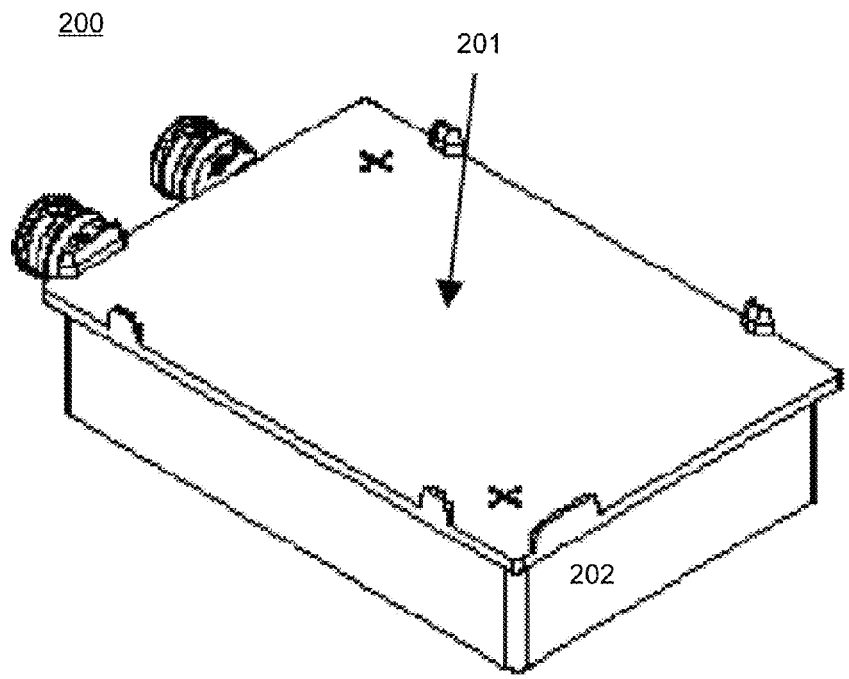
FIG. 2 illustrates a prior art cold plate.

Referring now to FIG. 2, previously known microtiter cold plates 200 had a top plate 201 that rested on top of an insulating layer 202, wherein the insulating layer 202 assisted to minimize condensation.

Figure 3:
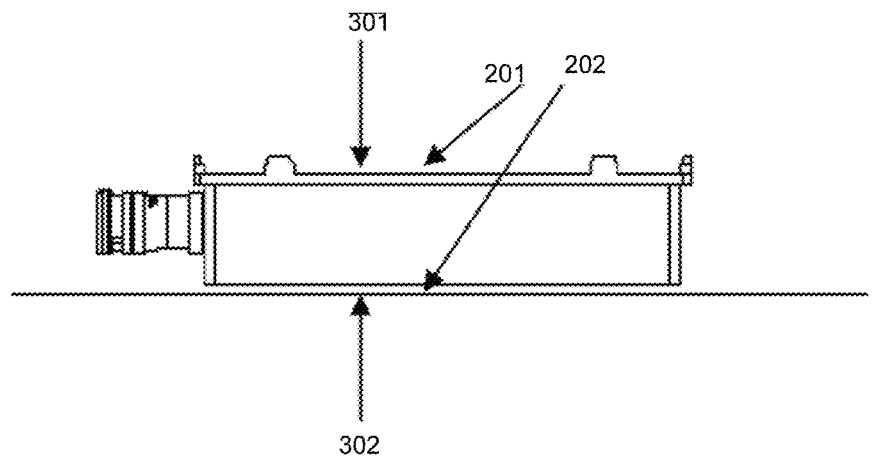
FIG. 3 illustrates a side of view of a prior art cold plate.

Referring now to FIG. 3, as described above, in prior art designs, condensation may be minimized by insulating areas of the cold plate 200 other than the top plate 201 with a plastic or foam insulation layer 202. However, the insulated layer 202 inconsistently affects alignment of the microtiter plate dimensions 301-302. It is very difficult to precisely machine or cut plastic or foam insulation 202. As a result, it is very difficult to maintain an insulated cold plate's precise thickness 301-302 and a parallelism between a plastic base with insulating layer 202 and metallic top plate 201 surface 301. This imprecision leads to positional variation across the cold plate surface relative to the cold plate's mounting base which in turn creates problems for alignment of robotic arms that commonly load the microtiter plates onto the cold plate. The insulating layer 202 was not sufficiently consistent in size and shape to provide for accurate placement of a microtiter plate on the surface.

Figure 4:
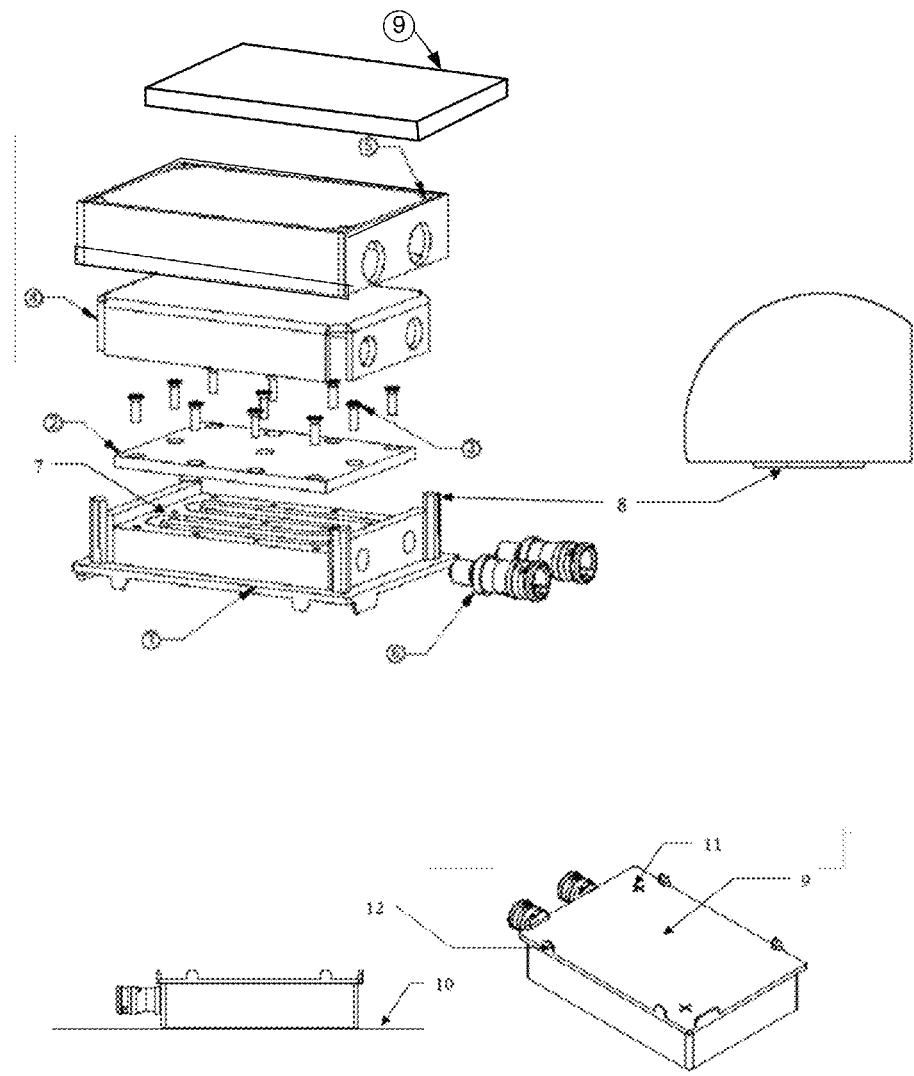
FIG. 4 illustrates a cold plate according to the present invention.

Referring now to FIG. 4, the present invention solves previously known microtiter cold plate problems by creating a rigid metal body 1 with legs 8 protruding through an insulation layer 4 and plastic cover 2. The precisely machined legs 8 overcome a problem of uniform thickness and parallelism associated with the insulation 4 and plastic cover 2 and allows precise vertical positioning of the top surface 5. Precise vertical positioning in turn facilitates rapid placement of microtiter plates by robotic arms.

According to the present invention, a single piece of, or a plurality of pieces of a thermally conductive material, such as a metal, is machined into the body of the microtiter cold plate 1. Some preferred materials for the microtiter cold plate 1 include aluminum and cooper. Interior water channels 7 provide for temperature control of a top plate 9 which is held in place via the alignment legs 8. The water channels 7 are sealed with cover plate 2 using either screws 3 to compress a gasketing material or via brazing. A lower metal body 1 is covered with insulation 4 followed by a rigid plastic cover 5, both glued in place. The alignment/support legs 8 integral to the microtiter cold plate 1 protrude through the plastic cover 5.

The alignment legs 8 provide vertical alignment and ensure the top surface 9 of the microtiter cold plate is parallel to mounting plate 10. Alignment marks 11 may also be included to allow x-y alignment of the robotic arm to the microtiter cold plate. Mechanical stops 12 ensure that the microtiter plate stays centered on the microtiter cold plate. In some preferred embodiments, the alignment support legs 8 protrude only slightly through the plastic cover thereby minimizing an exposed surface area where condensation or heat loss from the water channels 7 to an ambient environment could occur.

Further enhancements may include adding set screws to the bottom of each leg 8 for precise leveling, coating all exposed metal surfaces with a hydrophobic film to prevent condensation, and placing thin pieces of thermally insulating tape on the bottom of each support leg 8 to minimize thermal contact with the too support base 10.

Figure 5:
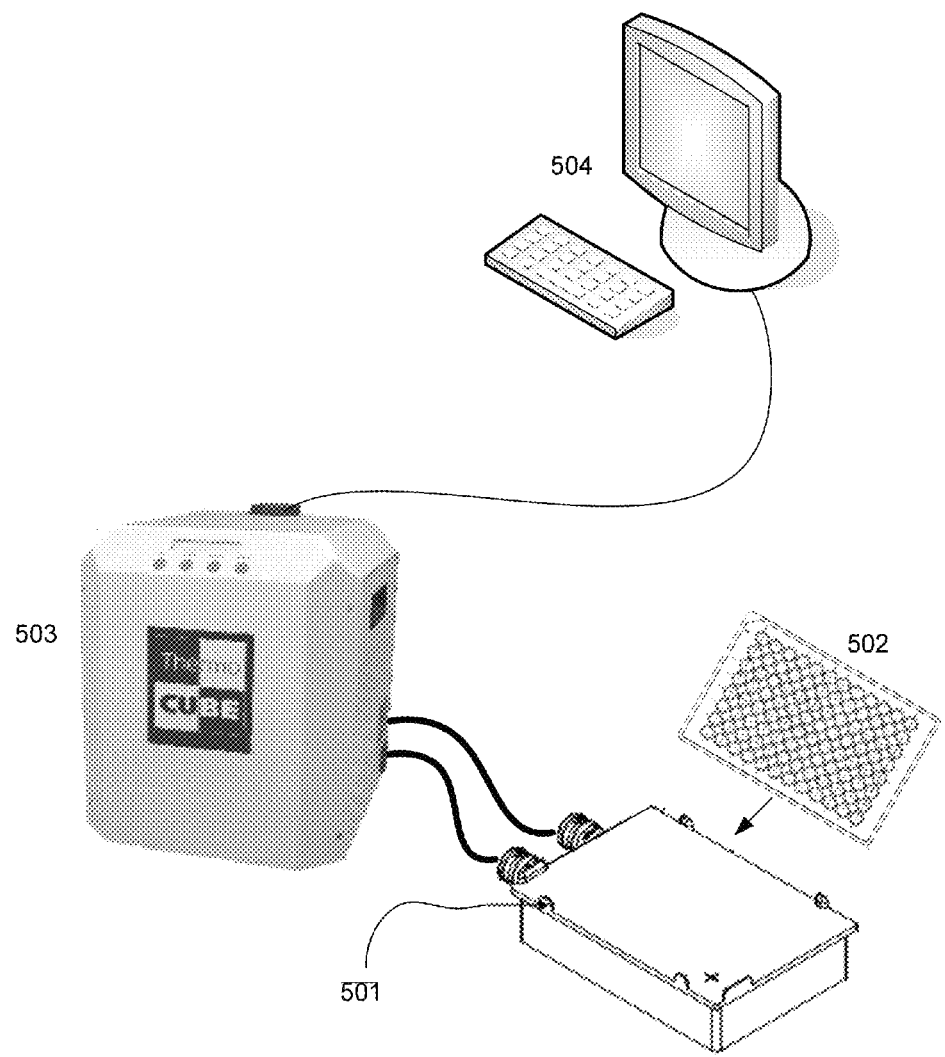
FIG. 5 illustrates a system for maintaining a temperature of a microtiter plate.

Referring now to FIG. 5, a system is illustrated to show a programmable controller 504 which is functional to control a temperature setting of a thermoelectric unit 503, such as, for example, a Thermo Cube by Solid State Cooling Company. The thermoelectric unit 503 controls the temperature of a coolant may be circulated through a cold plate 502 with alignment legs (not shown in FIG. 5). The cold plate 501 may then be used to control a temperature of a microtiter plate 502.

CONCLUSION

A number of embodiments of the present invention have been described. Nevertheless, it will be understood that various modifications may be made without departing from the spirit and scope of the invention. For example, various methods or equipment may be used to implement the process steps described herein or to create a device according to the inventive concepts provided above and further described in the claims. In addition, various data communication mechanisms and thermal transfer mechanisms may be utilized for various aspects of the present invention. Accordingly, other embodiments are within the scope of the following claims.

What is claimed is:

1. A microtiter cold plate assembly comprising:
    a microtiter cold plate rigid body comprising a single piece of metallic material, said rigid body comprising a flat top surface with several mechanical stops protruding from said top surface, said rigid body further comprising coolant channels in an opposite surface to the flat top surface and coolant fitting ports on one or more sides of said rigid body, said coolant fitting ports in fluid communication with said coolant channels,
    a cover plate sealing said coolant channels,
    insulation over all but the top surface, and
    support legs extending from the rigid body underside protruding through said insulation, said support legs comprising the single piece of metallic material of the rigid body.

2. The microtiter cold plate of claim 1 wherein the microtiter plate comprises between about 3 to 8 support legs.

3. The microtiter cold plate of claim 2, wherein the plate comprises 4 support legs.

4. The microtiter cold plate of claim 2, wherein the plate comprises 6 support legs.

5. The microtiter cold plate of claim 1 where the cover plate is welded to the rigid body.

6. The microtiter cold plate of claim 1 where the cover plate is brazed to the rigid body.

7. The microtiter cold plate of claim 1 where a sealant or gasket seals the cover plate to the rigid body.

8. The microtiter cold plate of claim 1 where an o-ring seal the cover plate to the rigid body.

9. The microtiter cold plate of claim 1 where the support legs protrude through the insulation by 0.5-3 mm, more commonly 0.5-1.5 mm, most commonly 1 mm.

10. The microtiter cold plate of claim 1 where the insulation comprises two parts, a flexible foamed plastic piece over the bottom and four sides of the rigid body and a hard plastic cover.

11. The microtiter cold plate of claim 1 where the coolant ports are located on one side.

12. The microtiter cold plate of claim 9 where the coolant ports are located at the top of the coolant channels.

13. The microtiter cold plate of claim 1 where the coolant ports are located on two separate sides.

14. The microtiter cold plate of claim 1 where the coolant channels form a serpentine pattern.

15. The microtiter cold plate of claim 1 where one or more alignment marks allow robotic arm's vision system X-Y alignment to the microtiter cold plate.

16. The microtiter cold plate of claim 1 where adjustment screws are inserted into the bottom of each leg to allow for precise leveling.

17. The microtiter cold plate of claim 1 where a layer of insulating tape is fixedly attached to the bottom of one or more support legs to minimize thermal conduction losses through a support leg to a support base.

18. The microtiter cold plate of claim 1 where a hydrophobic coating is applied to all exposed metal surfaces to prevent condensation.

* * * * *